(12) United States Patent
Kim

(10) Patent No.: US 10,575,885 B2
(45) Date of Patent: Mar. 3, 2020

(54) SCREW ANCHOR ASSEMBLY

(71) Applicant: KYUNGPOOK NATIONAL UNIVERSITY INDUSTRY-ACADEMIC COOPERATION FOUNDATION, Daegu (KR)

(72) Inventor: Kyoungtae Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 69 days.

(21) Appl. No.: 15/741,950

(22) PCT Filed: Jul. 11, 2016

(86) PCT No.: PCT/KR2016/007473
§ 371 (c)(1),
(2) Date: Jan. 4, 2018

(87) PCT Pub. No.: WO2017/010757
PCT Pub. Date: Jan. 19, 2017

(65) Prior Publication Data
US 2018/0199969 A1  Jul. 19, 2018

(30) Foreign Application Priority Data
Jul. 16, 2015  (KR) .................. 10-2015-0100783

(51) Int. Cl.
*A61B 17/84* (2006.01)
*A61B 17/70* (2006.01)
*A61B 17/86* (2006.01)

(52) U.S. Cl.
CPC ............ *A61B 17/844* (2013.01); *A61B 17/70* (2013.01); *A61B 17/7032* (2013.01);
(Continued)

(58) Field of Classification Search
CPC ....... A61B 17/84; A61B 17/844; A61B 17/86; A61B 17/8685; A61B 17/8625; A61B 17/70; A61B 17/7032
See application file for complete search history.

(56) References Cited

U.S. PATENT DOCUMENTS

| 4,027,932 | A | 6/1977 | Kunkel et al. |
| 4,359,318 | A | 11/1982 | Gittleman |

(Continued)

FOREIGN PATENT DOCUMENTS

| JP | 2011-139901 A | 7/2011 |
| JP | 2014-517739 A | 7/2014 |

(Continued)

*Primary Examiner* — Christopher J Beccia
(74) *Attorney, Agent, or Firm* — Novick, Kim & Lee, PLLC; Sang Ho Lee

(57) ABSTRACT

A screw anchor assembly is a screw anchor assembly used in spinal screw fixation, and includes a screw having screw threads in a lengthwise direction, and a screw anchor which is inserted into a predefined position of spine, and has anchor threads on an inner surface defining a receiving part into which the screw is inserted, the receiving part being expanded during screw coupling with the screw, wherein the screw anchor includes a plurality of divisions formed along a lengthwise direction, and has overlapping parts between adjacent divisions in the plurality of divisions.

10 Claims, 4 Drawing Sheets

(52) U.S. Cl.
CPC .......... *A61B 17/86* (2013.01); *A61B 17/8625* (2013.01); *A61B 17/8685* (2013.01); *A61B 17/866* (2013.01); *A61B 2017/8655* (2013.01)

(56) References Cited

U.S. PATENT DOCUMENTS

| | | | |
|---|---|---|---|
| 4,474,516 | A | 10/1984 | Schiefer |
| 4,678,383 | A | 7/1987 | Bergner |
| 5,127,407 | A | 7/1992 | Tan |
| 5,265,504 | A | 11/1993 | Fruhm |
| 6,171,311 | B1 | 1/2001 | Richelsoph |
| 6,249,946 | B1 | 6/2001 | Greenhill |
| 6,258,089 | B1 | 7/2001 | Campbell et al. |
| 6,290,701 | B1 | 9/2001 | Enayati |
| 6,331,179 | B1 | 12/2001 | Freid et al. |
| 6,402,757 | B1 | 6/2002 | Moore, III et al. |
| 6,436,100 | B1 | 8/2002 | Berger |
| 6,652,525 | B1 | 11/2003 | Assaker et al. |
| 6,767,350 | B1 * | 7/2004 | Lob .................. A61B 17/68 606/326 |
| 6,778,861 | B1 | 8/2004 | Liebrecht et al. |
| 7,029,472 | B1 | 4/2006 | Fortin |
| 7,194,314 | B1 | 3/2007 | Richter et al. |
| 7,235,100 | B2 | 6/2007 | Martinek |
| 7,302,298 | B2 | 11/2007 | Lowry et al. |
| 7,662,154 | B2 | 2/2010 | Ribeiro |
| 8,057,521 | B2 | 11/2011 | Smisson, III et al. |
| 8,419,777 | B2 | 4/2013 | Walker et al. |
| 8,454,667 | B2 | 6/2013 | Humphreys |
| 8,628,325 | B2 | 1/2014 | Vachtenberg |
| 8,758,347 | B2 | 6/2014 | Weiner et al. |
| 8,906,077 | B2 | 12/2014 | Bush, Jr. |
| 8,932,335 | B2 | 1/2015 | Humphreys |
| 8,940,030 | B1 | 1/2015 | Stein et al. |
| 8,956,394 | B1 | 2/2015 | McDonnell |
| 9,265,531 | B2 | 2/2016 | Ziolo |
| 9,629,664 | B2 | 4/2017 | Altarac et al. |
| 9,775,652 | B2 | 10/2017 | Altarac et al. |
| 9,918,749 | B2 | 3/2018 | Altarac et al. |
| 9,918,760 | B2 | 3/2018 | Bush, Jr. et al. |
| 9,943,341 | B2 | 4/2018 | Carnes et al. |
| 2002/0040241 | A1 | 4/2002 | Jarvinen |
| 2002/0151899 | A1 | 10/2002 | Bailey et al. |
| 2003/0135274 | A1 | 7/2003 | Hays et al. |
| 2003/0187440 | A1 | 10/2003 | Richelsoph et al. |
| 2004/0220571 | A1 | 11/2004 | Assaker et al. |
| 2004/0243207 | A1 | 12/2004 | Olson et al. |
| 2004/0267361 | A1 | 12/2004 | Donnelly et al. |
| 2005/0059972 | A1 | 3/2005 | Biscup |
| 2005/0192577 | A1 | 9/2005 | Mosca et al. |
| 2005/0216027 | A1 | 9/2005 | Suh |
| 2005/0261689 | A1 | 11/2005 | Lin |
| 2006/0106390 | A1 | 5/2006 | Jensen et al. |
| 2006/0149258 | A1 | 7/2006 | Sousa |
| 2006/0161157 | A1 | 7/2006 | Mosca et al. |
| 2006/0217721 | A1 | 9/2006 | Suh |
| 2006/0235410 | A1 | 10/2006 | Ralph et al. |
| 2006/0247639 | A1 | 11/2006 | Anderson |
| 2006/0293670 | A1 | 12/2006 | Smisson et al. |
| 2007/0233071 | A1 | 10/2007 | Dewey et al. |
| 2008/0161864 | A1 | 7/2008 | Beck et al. |
| 2008/0188897 | A1 | 8/2008 | Krebs et al. |
| 2008/0221624 | A1 | 9/2008 | Gooch |
| 2009/0125072 | A1 | 5/2009 | Neubardt |
| 2009/0318970 | A1 | 12/2009 | Butler et al. |
| 2010/0036467 | A1 | 2/2010 | Kraus et al. |
| 2010/0049256 | A1 | 2/2010 | Jeon et al. |
| 2010/0106198 | A1 | 4/2010 | Adcox et al. |
| 2010/0121383 | A1 | 5/2010 | Stanaford et al. |
| 2011/0022097 | A1 | 1/2011 | Walker et al. |
| 2011/0029023 | A1 | 2/2011 | Tornier |
| 2011/0106159 | A1 | 5/2011 | Nazeck |
| 2011/0144702 | A1 | 6/2011 | Leroux et al. |
| 2011/0152934 | A1 | 6/2011 | Asaad et al. |
| 2011/0230885 | A1 | 9/2011 | Weiner et al. |
| 2011/0264151 | A1 | 10/2011 | Davis et al. |
| 2012/0185001 | A1 | 7/2012 | Nayet et al. |
| 2012/0232595 | A1 | 9/2012 | Holschlag |
| 2012/0265258 | A1 * | 10/2012 | Garvey .............. A61B 17/8685 606/315 |
| 2012/0271363 | A1 | 10/2012 | Luxon et al. |
| 2012/0289978 | A1 | 11/2012 | Jacob |
| 2013/0023936 | A1 | 1/2013 | Altarac et al. |
| 2013/0041413 | A1 | 2/2013 | Sun |
| 2013/0231704 | A1 | 9/2013 | Larroque-Lahitette |
| 2013/0304067 | A1 | 11/2013 | Hess et al. |
| 2013/0325074 | A1 | 12/2013 | Ziolo |
| 2014/0066997 | A1 | 3/2014 | Humphreys |
| 2015/0134013 | A1 | 5/2015 | Paul |
| 2015/0201982 | A1 | 7/2015 | Altarac et al. |
| 2015/0216573 | A1 | 8/2015 | Chin et al. |
| 2015/0230838 | A1 | 8/2015 | Lazoglu et al. |
| 2016/0166295 | A1 | 6/2016 | Ziolo |
| 2016/0206351 | A1 | 7/2016 | Eom |

FOREIGN PATENT DOCUMENTS

| | | |
|---|---|---|
| KR | 1999-0035953 A | 5/1999 |
| KR | 10-2002-0082009 A | 10/2002 |
| KR | 1020040001287 A | 1/2004 |
| KR | 20-0367241 Y1 | 11/2004 |
| KR | 10-2005-0023111 A | 3/2005 |
| KR | 10-2007-0026472 A | 3/2007 |
| KR | 10-2007-0112200 A | 11/2007 |
| KR | 10-2008-0059920 A | 7/2008 |
| KR | 10-0850322 B1 | 8/2008 |
| KR | 10-2008-0105506 A | 12/2008 |
| KR | 10-0872529 B1 | 12/2008 |
| KR | 10-2009-0015933 A | 2/2009 |
| KR | 10-2009-0111774 A | 10/2009 |
| KR | 10-2010-0124709 A | 11/2010 |
| KR | 10-2012-0039622 A | 4/2012 |
| KR | 10-2012-0040309 A | 4/2012 |
| KR | 10-2012-0052265 A | 5/2012 |
| KR | 10-1142895 B1 | 5/2012 |
| KR | 10-2012-0057758 A | 6/2012 |
| KR | 10-2013-0004669 A | 1/2013 |
| KR | 10-2013-0015081 A | 2/2013 |
| KR | 10-2013-0016303 A | 2/2013 |
| KR | 10-1331429 B1 | 11/2013 |
| KR | 10-2014-0003938 A | 1/2014 |
| KR | 10-2014-0018796 A | 2/2014 |
| KR | 10-2014-0052320 A | 5/2014 |
| KR | 10-1413732 B1 | 7/2014 |
| KR | 10-2015-0120105 A | 10/2015 |
| WO | 2008/146981 A1 | 12/2008 |
| WO | 2009/105106 A2 | 8/2009 |

* cited by examiner

SCREW ANCHOR ASSEMBLY

TECHNICAL FIELD

The present disclosure relates to a screw anchor assembly, and more particularly, to a screw anchor assembly with a structure for increasing a contact area with vertebra.

BACKGROUND ART

Generally, in the treatment of spine related diseases, indirect treatment methods through physical therapy and direct treatment methods that adjust and fix the spine by mounting a separate fixing device into a damaged part of the spine are performed. That is, in the case of mild spinal diseases, physical therapy is performed, but in the case of severe diseases in the cervical vertebrae, thoracic vertebrae, lumbar vertebrae, sacrum and intervertebral disk that make up the spine, treatments are conducted using a separate spine fixing device.

Commonly used spine fixing devices include a pedicle (sacral) screw that is inserted into the pedicle or sacrum of the vertebra at a predefined angle and depth, a spinal rod that is disposed on one side of the part of the spine, and a fixing cap or a coupling fastener that fastens the spinal rod and the pedicle screw together, in order to adjust the damaged part of the spine to the normal condition and fix it without movement. To treat the damaged part of the spine, the pedicle screw is first inserted into and fixed onto the pedicle or the sacrum of vertebra in an appropriate orientation and position, then the part of the spine is adjusted to normal condition using the spinal rod, and lastly, the spinal rod and the fixing screw are secured using the fixing cap or coupling fastener, completing the treatment.

Meanwhile, recently, with the aging population, screw fixation is increasingly used for patients with severe osteoporosis. However in the case of conventional screw fixation (Korean Patent Application No. 10-2006-0133857), after the screw fixation is performed, the bones around the screw fixed to the bone may resolve over time, otherwise known as halo, a bone cavitation phenomenon which causes a screw loosening phenomenon. Consequently, nearly half of the patients who undergo the screw insertion may experience adjacent segment degeneration as a screw fixation aftermath, requiring reoperation which becomes a physical and economic burden to the patients.

In this case, a larger screw may be inserted into the position at which the screw loosening phenomenon occurred, or the bones around the screw may be filled with cement or transplanted with allograft bone plug. However, it was previously difficult to obtain secure fixation of the screw into the bone through this method.

DISCLOSURE

Technical Problem

To solve this problem, there is a need for a screw anchor assembly preventing the screw loosening phenomenon from occurring after screw fixation.

The present disclosure is directed to providing a screw anchor assembly that increases a contact area with the vertebra and has sufficient pull-out strength, thereby achieving secure screw fixation and reducing the patients' physical and economic burden.

The problems intended to solve by the present disclosure are not limited to the problems mentioned above, and other problems not stated herein will be apparent from the following description.

Technical Solution

To solve the problem, a screw anchor assembly according to an embodiment of the present disclosure is a screw anchor assembly used in spinal screw fixation, and includes a screw assembly having screw threads in a lengthwise direction, and a screw anchor which is inserted into a predefined position of spine, and has anchor threads on an inner surface defining a receiving part into which the screw is inserted, of which the receiving part being expanded during screw coupling with the screw, wherein the screw anchor includes a plurality of divisions formed along a lengthwise direction, and has overlapping parts between adjacent divisions in the plurality of divisions.

Advantageous Effects

According to the present disclosure, it is possible to provide a screw anchor assembly that increases a contact area with vertebra and has sufficient pull-out strength, thereby achieving secure screw fixation and reducing patients' physical and economic burden.

Figure 1:
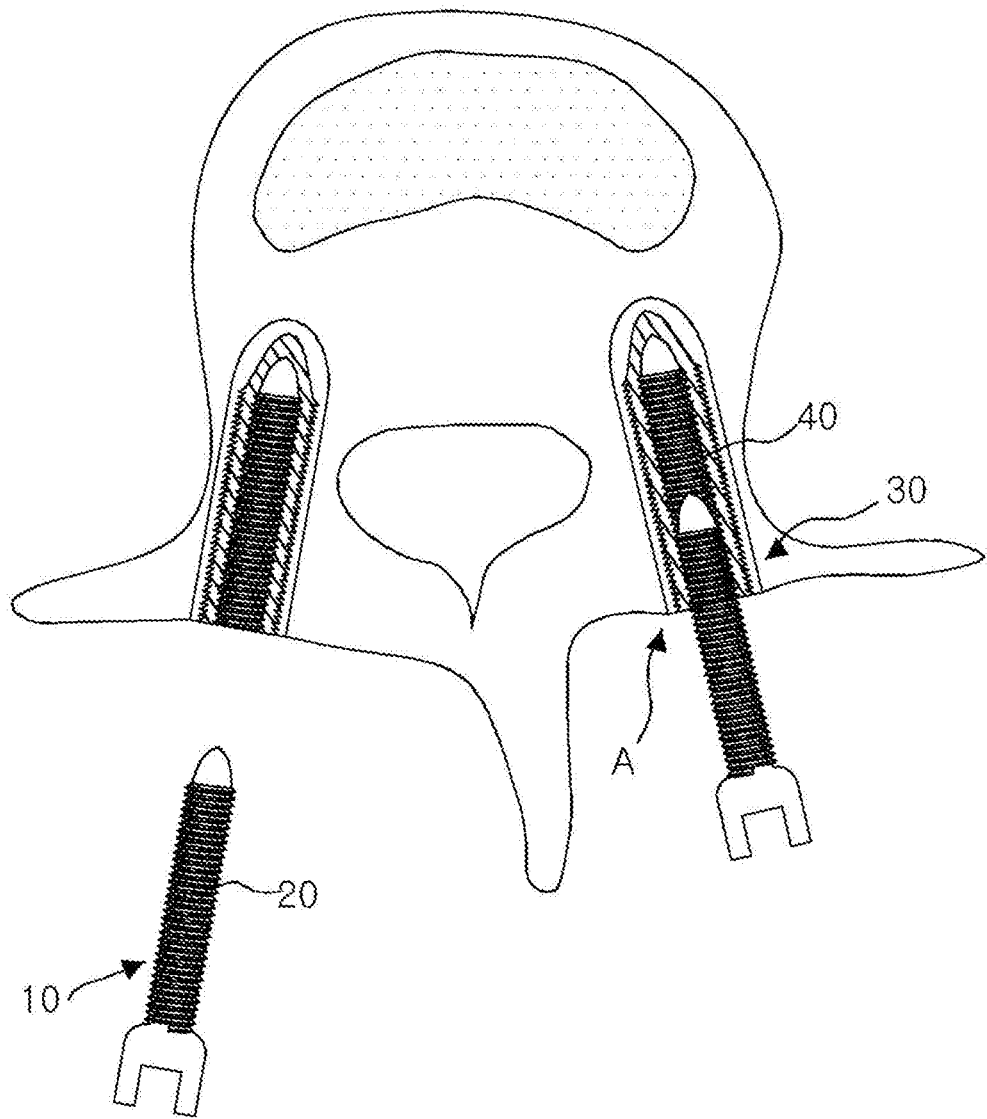
FIG. 1 is a diagram showing a process of fixing a screw anchor assembly into the vertebra according to an embodiment of the present disclosure.

| <Detailed Description of Main Elements> | |
|---|---|
| 10: Screw | 20: Screw threads |
| 30, 100: Screw anchor | 40: Anchor threads |
| 50: Receiving part | 60: One end of threaded anchor |
| 70: Stopper part | 80: Connecting part |
| 91, 92, 93, 94: Division | |

BEST MODE

These advantages and features of the present disclosure and the methods for achieving them will be apparent from the embodiments described in detail below in conjunction with the accompanying drawings. However, the present disclosure is not limited to the following disclosed embodiments and will be embodied in many different forms, and these embodiments are only provided to make the disclosure complete and help those having ordinary skill in the technical field pertaining to the present disclosure to understand the scope of the invention fully, and the present disclosure is only defined by the scope of the appended claims. Like reference numerals indicate like elements throughout the specification.

The terminology used herein is for the purpose of describing the embodiments only and is not intended to be limiting of the present disclosure. As used herein, the singular forms are intended to include the plural forms as well, unless the context clearly indicates otherwise. The term "comprises" and/or "comprising" when used in this specification specifies the presence of stated elements, steps, and operations, but do not preclude the presence or addition of one or more other elements, steps, and operations.

Figure 2:
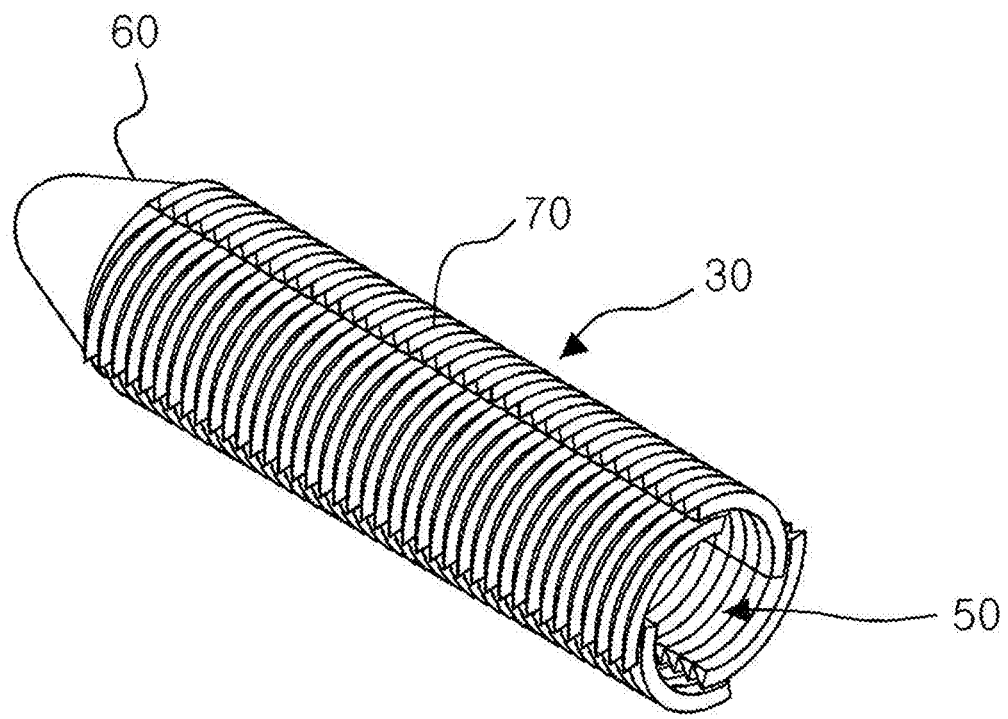
FIG. 2 is a schematic perspective view of a screw anchor of a screw anchor assembly according to an embodiment of the present disclosure.
Figure 3:
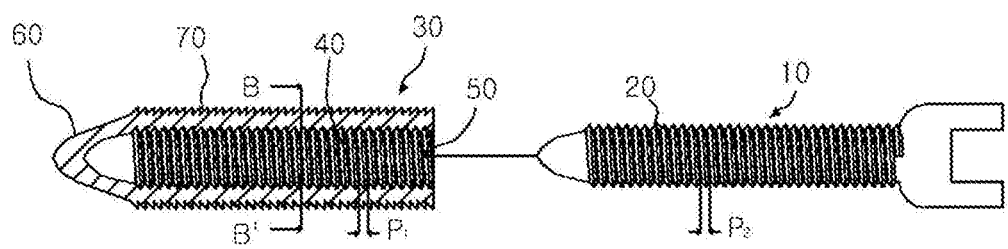
FIG. 3 is a horizontal cross-sectional view of a screw anchor assembly according to an embodiment of the present disclosure.
Figure 4:
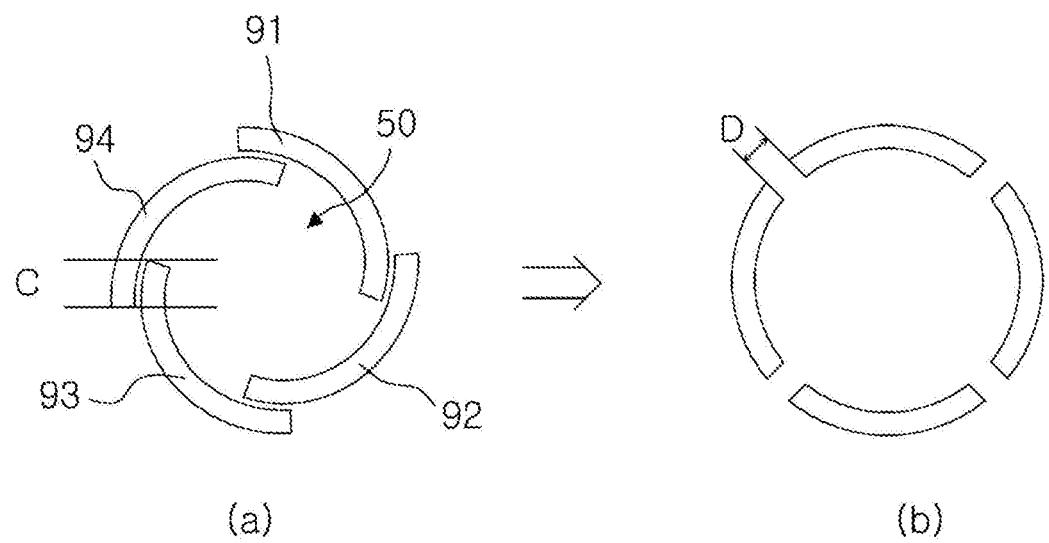
FIG. 4 is a cross-sectional view taken along the line B-B' of FIG. 3.

A screw anchor assembly according to an embodiment of the present disclosure is described with reference to FIGS. 1 to 4. FIG. 1 is a diagram showing a process of fixing the screw anchor assembly into the vertebra according to an embodiment of the present disclosure. FIG. 2 is a schematic perspective view of a screw anchor of the screw anchor assembly according to an embodiment of the present disclosure. FIG. 3 is a horizontal cross-sectional view of the screw anchor assembly according to an embodiment of the present disclosure. FIG. 4 is a cross-sectional view taken along the line B-B' of FIG. 3.

Referring to FIGS. 1 to 4, the screw anchor assembly according to an embodiment of the present disclosure includes a screw anchor 30 and a screw 10.

The screw anchor 30 is an element that is inserted into a predefined position of vertebra first instead of inserting the screw 10 directly, and allows the screw 10 to be inserted into a receiving part 50 inside to enable more secure fixation of the screw 10 into vertebra. To support this, the screw anchor 30 has the receiving part 50 that receives the screw 10 therein in the lengthwise direction, and one end 60 that is inserted into vertebra is in a pointed conic shape to effectively insert the screw anchor 30 into vertebra.

Anchor threads 40 are formed on an inner surface defining the receiving part 50 of the screw anchor 30, and the anchor threads 40 may be screw-coupled with screw threads 20 of the screw 10 as described below, and through this screw coupling, the screw 10 is received in the screw anchor 30. Meanwhile, the pitch $P_1$ of the anchor threads 40 is equal to the pitch $P_2$ of the screw threads 20 to prevent damage of the screw anchor 30 and/or the screw 10 when the screw 10 is inserted into the screw anchor 30 through screw coupling.

Additionally, the screw anchor 30 is composed of a plurality of divisions 91, 92, 93, 94 formed along the lengthwise direction, a space formed by one end 60 of the screw anchor 30 and the plurality of divisions 91, 92, 93, 94 connected to one end 60, i.e., an inner part surrounded by the plurality of divisions 91, 92, 93, 94 becomes the receiving part 50, and in normal condition before the screw anchor 30 is inserted into vertebra, there are overlapping parts C between adjacent divisions. By this structure, when the screw 10 is inserted into the screw anchor 30 through screw coupling, and accordingly, the receiving part 50 of the screw anchor 30 is expanded, the distance D between adjacent divisions becomes closer compared to conventional anchors, and thus an area of vertebra that does not touch the screw anchor 30 reduces.

Accordingly, fixation of the screw anchor assembly into vertebra is semi-permanent and more secure, thereby producing effects on the reductions in reoperation rate and patients' physical and economic burden.

Further, a stopper part 70 may be formed on the outer surface of the divisions 91, 92, 93, 94 of the screw anchor 30, and the stopper part 70 may be formed along the lengthwise direction of the screw anchor 30, and may be formed on the outer surface of the divisions 91, 92, 93, 94 in whole or in part. Furthermore, the stopper part 70 may have a slope surface, and the slope surface may slope toward one end 60 of the screw anchor 30.

As described above, as the stopper part 70 is formed on the outer surface of the divisions 91, 92, 93, 94, the friction coefficient and contact area of the screw anchor 30 with the bone surface increases and sufficient pull-out strength can be obtained, which as a result, can prevent the screw 10 inserted into the screw anchor 30 from slipping out of the bone.

For a material of the screw anchor 30, any material that is not harmful to human body is available, and a plastic material such as poly(methylmethacrylate) (PMMA) may be used, but recently development using calcium phosphate is in progress, and polyether ether ketone (PEEK), bone material (or bone substitute material; material that is transformed into bone over time) or artificial bone is available. As the screw anchor 30 is made of this material, during insertion of the screw 10, the screw anchor 30 expands and fills the space within the bone, thereby improving the fixation strength of the screw 10.

The screw 10 is a type of nail having the screw threads 20 formed in the lengthwise direction, and when it is inserted into the screw anchor 30 through screw coupling, it expands the receiving part 50 of the screw anchor 30, and accordingly, the screw anchor 30 is fixed into the vertebra. As a result, fixation of the screw anchor 30 produces an effect on the fixation of the screw 10 into vertebra, thereby maintaining the spine in a desired shape.

As described above, because the pitch of the screw threads 20 is equal to the pitch of the anchor threads 40, damage of the screw anchor 30 and/or the screw 10 can be prevented when the screw 10 is inserted into the screw anchor 30 through screw coupling.

Additionally, for a material of the screw 10, any material that is not harmful to human body is available similar to the screw anchor 30, and a plastic material such as poly(methylmethacrylate) (PMMA) may be used, but recently development using calcium phosphate is in progress, and polyether ether ketone (PEEK), bone material (or bone substitute material; material that is transformed into bone over time) or artificial bone is available.

As shown in FIG. 1, spinal screw fixation is performed using the screw anchor assembly including the screw anchor 30 and the screw 10 described above, and specifically, to treat the damaged part of the spine, the screw anchor 30 is inserted and fixed into the pedicle or sacrum of vertebra in appropriate orientation and position first, and the screw 10 is screw coupled to the receiving part 50 of the inserted screw anchor 30 using a drive (not shown).

Figure 5:
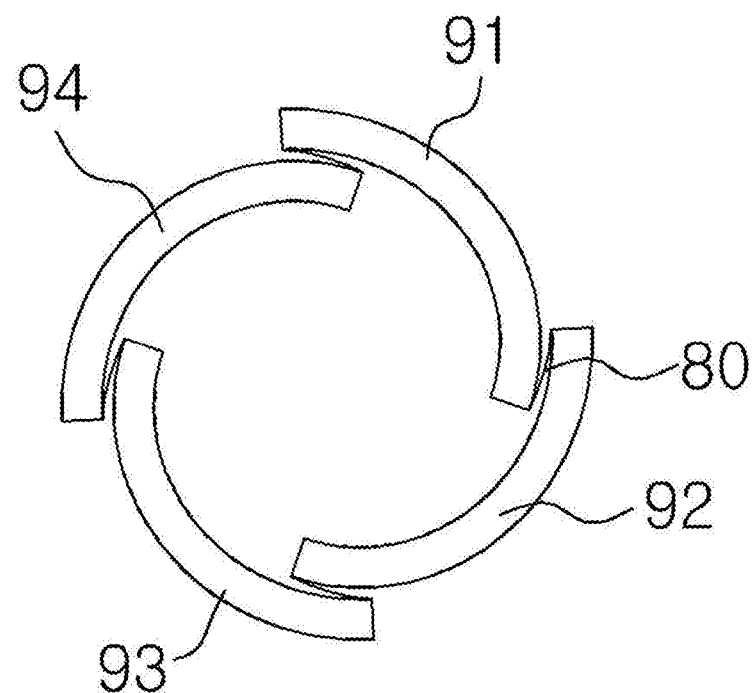
FIG. 5 is a vertical cross-sectional view of a screw anchor of a screw anchor assembly according to another embodiment of the present disclosure.

The screw anchor assembly according to an embodiment of the present disclosure has been hereinabove described, and a screw anchor assembly according to another embodiment of the present disclosure is described below with reference to FIG. 5. FIG. 5 is a vertical cross-sectional view of a screw anchor of the screw anchor assembly according to another embodiment of the present disclosure.

Referring to FIG. 5, the screw anchor assembly according to another embodiment of the present disclosure further includes a connecting part 80 connecting the divisions 91, 92, 93, 94 of the screw anchor 30.

The plurality of divisions 91, 92, 93, 94 that makes up the screw anchor 30 is separated with overlapping parts C therebetween, but adjacent divisions are connected by the connecting part 80 and thus have parts not separated from each other.

The connecting part 80 may connect the parts of adjacent divisions, and some or all adjacent divisions may have the connection of the connecting part 80.

When the screw 10 is screw coupled to and inserted into the screw anchor 30 in the presence of the connecting part 80, as the distance between the plurality of divisions 91, 92, 93, 94 increases, the connecting part 80 connecting adjacent divisions is disconnected and the space of the receiving part 50 is expanded.

Meanwhile, because the screw anchor assembly according to another embodiment of the present disclosure includes the divisions 91, 92, 93, 94 connected by the connecting part 80 as described above, when it is in normal condition, the plurality of divisions 91, 92, 93, 94 is placed in fixed position relative to each other, and accordingly the screw anchor 30 can maintain its original shape.

Figure 6:
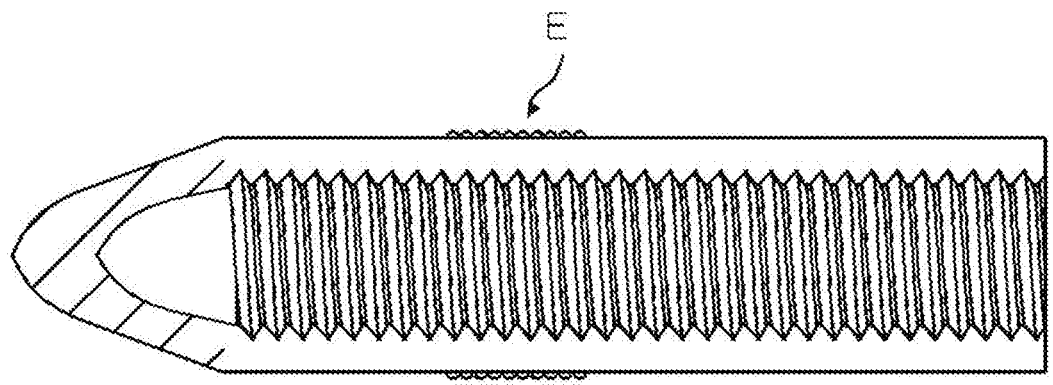
FIG. 6 is a horizontal cross-sectional view of a screw anchor of a screw anchor assembly according to still another embodiment of the present disclosure.

The screw anchor assemblies according to an embodiment and another embodiment of the present disclosure have been hereinabove described, and a screw anchor assembly according to still another embodiment of the present disclosure is described below with reference to FIG. 6. FIG. 6 is a horizontal cross-sectional view of a screw anchor of the screw anchor assembly according to still another embodiment of the present disclosure.

Referring to FIG. 6, the surface of the screw anchor 30 (i.e., the outer surface of the plurality of divisions) is roughening treated, and thus the screw anchor 30 includes a rough outer surface E.

By this roughening treated outer surface E, the friction coefficient of the screw anchor 30 with the bone surface increases, sufficient pull-out strength is obtained, and the fixation strength of the screw anchor 30 is enhanced. Furthermore, the rough outer surface E having undergone surface roughening treatment may be formed on the surface of the screw anchor 30 in whole or in part.

Figure 7A:
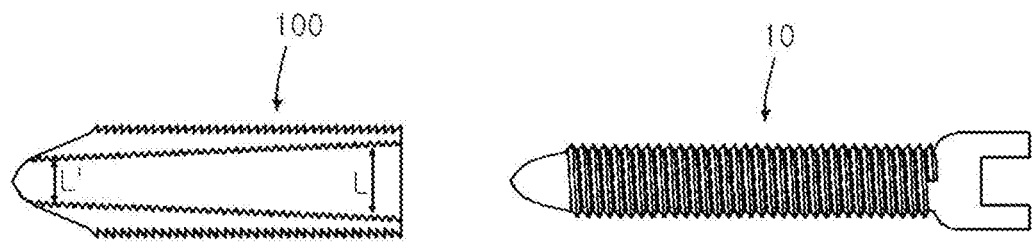
FIGS. 7A and 7B are horizontal cross-sectional views of a screw anchor assembly according to yet another embodiment of the present disclosure.
Figure 7B:
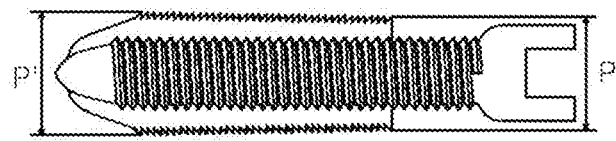

The screw anchor assemblies according to an embodiment, another embodiment and still another embodiment of the present disclosure have been hereinabove described, and a screw anchor assembly according to yet another embodiment of the present disclosure is described below with reference to FIGS. 7A and 7B. FIGS. 7A and 7B are horizontal cross-sectional views of the screw anchor assembly according to yet another embodiment of the present disclosure.

A screw anchor 100 of the screw anchor assembly according to yet another embodiment of the present disclosure has the internal receiving part becoming narrower as it goes to one end that is inserted into the bone earlier. That is, as can be seen through FIG. 7A, the diameter L' of the receiving part at the side of one end of the screw anchor 100 is smaller than the diameter L of the receiving part at the side of the other end opposite to one end.

Additionally, as can be seen through FIG. 7B, because the receiving part of the screw anchor 100 becomes narrower as it goes to one end, when the screw 10 is inserted into the screw anchor 100, as it goes to the narrower end, the extent to which the screw anchor 100 spreads outward becomes greater, i.e., the outer diameter P' of the screw anchor 100 at the side of one end becomes larger than the outer diameter P of the screw anchor 100 at the side of the other end, and thus the bond strength of the bone and the screw anchor 100 is further enhanced.

As mentioned above, conventionally, there has been a problem that after screw fixation is performed, a screw loosening phenomenon occurs over time, requiring reoperation, but the conventional problem can be solved by enabling secure fixation of the screw into bone using the screw anchor assembly according to the present disclosure as described above.

While the embodiments of the present disclosure have been hereinabove described with reference to the accompanying drawings, it will be appreciated by those having ordinary skill in the technical field pertaining to the present disclosure that the present disclosure may be embodied in other specific forms without changing the technical spirit or essential features of the present disclosure. Therefore, it should be understood that the embodiments described above are for illustration purposes only in all aspects, but not intended to be limiting.

The invention claimed is:

1. A screw anchor assembly used in spinal screw fixation, the screw anchor assembly comprising:
a screw having screw threads; and
a screw anchor which has anchor threads on an inner surface defining a receiving part into which the screw is inserted, the receiving part being expanded while the screw is being inserted,
wherein the screw anchor has a first end, and a plurality of division protrusions extended along a longitudinal direction from the first end, and adjacent division protrusions of the plurality of division protrusions have overlapped areas,
wherein the screw anchor further comprises a plurality of connection parts connecting the adjacent division protrusions of the plurality of division protrusions, and
wherein at least a part of the plurality of connection parts are configured to be broken while the receiving part is being expanded.

2. The screw anchor assembly according to claim 1, wherein a stopper part is protruded on an outer surface of the plurality of division protrusions.

3. The screw anchor assembly according to claim 2, wherein the stopper part has a slope surface, and the slope surface slopes toward the first end of the screw anchor.

4. The screw anchor assembly according to claim 2, wherein the stopper part is defined on at least a part of the outer surface of the plurality of division protrusions.

5. The screw anchor assembly according to claim 1, wherein at least a part of an outer surface of the plurality of division protrusions has an uneven area.

6. The screw anchor assembly according to claim 1, wherein a pitch of the screw threads and a pitch of the anchor threads have the same value.

7. The screw anchor assembly according to claim 1, wherein the first end has a pointed conic shape.

8. The screw anchor assembly according to claim 7, wherein the receiving part is defined by the first end and the plurality of division protrusions.

9. The screw anchor assembly according to claim 1, wherein a cross-section of the receiving part has a reduced diameter as the cross-section of the receiving part is closely located to the first end.

10. The screw anchor assembly according to claim 9, wherein a cross-section of the screw threads of the screw has a uniformed diameter.

* * * * *